United States Patent [19]
Huff et al.

[11] Patent Number: 5,661,040
[45] Date of Patent: Aug. 26, 1997

[54] FLUORESCENT POLYMER LABELED CONJUGATES AND INTERMEDIATES

[75] Inventors: Jeffrey B. Huff, Park Ridge; Christopher Bieniarz, Highland Park; Wayne J. Horng, Glenview, all of Ill.

[73] Assignee: Abbott Laboratories, Abbott Park, Ill.

[21] Appl. No.: 324,004

[22] Filed: Oct. 14, 1994

Related U.S. Application Data

[63] Continuation-in-part of Ser. No. 270,285, Jul. 11, 1994, abandoned, which is a continuation-in-part of Ser. No. 91,149, Jul. 13, 1993, abandoned.

[51] Int. Cl.$^6$ ............... G01N 33/545; G01N 33/533; C07K 17/00
[52] U.S. Cl. ............... 436/531; 435/6; 435/7.21; 435/7.24; 435/960; 436/532; 436/547; 530/391.3
[58] Field of Search ............... 436/532, 531, 436/547; 435/6, 7.21, 7.24, 960; 530/391.3

[56] References Cited

U.S. PATENT DOCUMENTS

| | | | |
|---|---|---|---|
| 4,166,105 | 8/1979 | Hirschfeld . | |
| 4,169,137 | 9/1979 | Hirschfeld et al. . | |
| 4,331,808 | 5/1982 | Buckler et al. | 544/234 |
| 4,452,886 | 6/1984 | Henry | 435/188 |
| 4,604,364 | 8/1986 | Kosak | 436/501 |
| 4,645,646 | 2/1987 | Gadow et al. | 436/535 |
| 4,670,406 | 6/1987 | Allen et al. | 436/532 |
| 4,906,579 | 3/1990 | Yalpani et al. | 536/56 |
| 5,032,518 | 7/1991 | Huber et al. | 435/188 |
| 5,106,762 | 4/1992 | Bredehorst et al. | 436/546 |
| 5,173,481 | 12/1992 | Pitha et al. | 514/58 |
| 5,183,809 | 2/1993 | Weisz et al. | 530/810 |
| 5,183,883 | 2/1993 | Tanaka et al. | 536/112 |
| 5,208,316 | 5/1993 | Yoshinaga | 528/364 |

FOREIGN PATENT DOCUMENTS

| | | |
|---|---|---|
| 0447133A2 | 3/1991 | European Pat. Off. . |
| 2238384A | 5/1991 | United Kingdom . |
| WO91/02040 | 2/1991 | WIPO . |
| WO92/20746 | 11/1992 | WIPO . |

OTHER PUBLICATIONS

Synthesis of Chemically Modified Cyclodextrins Alan P. Croft, et al *Tetrahedron*, vol. 39, No. 9, 1417–1474 (1983).
Synthesis and Characterization of Novel Multi–Functional Host Compounds, 3.β–Cyclodextrin Derivatives Bearing Schiff Base Moiety Bao–Jian Shen, Lin–Hui Tong, Dao–Sen Jin *Synthetic Communications*, 21(5), 635–641 (1991).
A Mild Process for the Oxidation of Partially Protected Carbohydrates Roger W. Binkley *J. Org. Chem.*, vol. 42, No. 7, 1216–1221 (1977).
Synthesis of α,β–Unsaturated, Carbonyl Sugar Derivatives By Methyl Sulfoxide Oxidation and Elmination D. M. Mackie and A. S. Perlin *Carbohydrate Research*, 24, 67–85 (1972).
Cooperative Binding by Aggregated Mono–6–(alkylamino)–β–cyclodextrins Russell C. Petter, Jeffrey S. Salek, Christopher T. Sikorski, G. Kumaravel, and Fu–Tyan Lin *J. Am. Chem. Soc.*, 112, 3860–3868 (1990).
Attachment of Fluorescent Dyes to Polyacrylamides in Aqueous Media Robert Borg and Mitchell A. Winnik *J. of Polymer Science: Part A: Polymer Chemistry*, vol. 28, 2075–2083 (1990).
Fluoroimmunoassy of 5α–Dihydrotestosterone D. Exley and G. I. Ekeke *J. of Steroid Biochemistry*, vol. 14, 1297–1302 (1981).
ω–Aldehydo Sugars Prepared by Ninhydrin Oxidation Alan R. Gibson, Laurence D. Melton, and Keith N. Slessor *Can J. Chem.*, vol. 52, 3905–3912 (1974).
Interaction of Cyclodextrin–Containing Polymers with Fluorescent Compounds Akira Harada, Masaoki Furue, and Shun–ichi Nozakura *Macromolecules*, vol. 10, No. 3, 676–681 (May–Jun. 1977).
Cyclodextrin–Containing Polymers Akira Harada, Masaoaki Furue, and Shun–ichi Nozakura *Macromolecules*, vol. 9, No. 5, 701–704 (Sep. –Oct. 1976).
Lasing of Rhodamine B in Aqueous Solutions Containing β–Cyclodextrin Yinon Degani, Itamar Willner *Chemical Physics Letters*, vol. 104, No. 5, 496–499 (17 Feb. 1984).
Preparation of Unsubstituted 6–Aldehydocelluloses by Photolysis of 6–Azido–6–Deoxycelluloses Derek Horton, Arthur E. Luetzow, and Olof Theander *Carbohydrate Research*, 26, 1–19 (1973).
Cyclodextrins in Diagnostics Josef Szejtli *Kontakte*, vol. 1, 31–36 (1988).

*Primary Examiner*—Mary E. Ceperley
*Attorney, Agent, or Firm*—David L. Weinstein; Paul D. Yasger

[57] ABSTRACT

The instant invention provides a highly fluorescent conjugate which is useful in specific binding assays, and which comprises a specific binding member bound to a fluorescent polymer. The fluorescent polymer comprises a backbone polymer having multiple signal generating groups immobilized thereon and, optionally, cyclodextrin moieties in association with the polymer. Also provided is a novel process for creating 6-cyclodextrin monoaldehyde.

15 Claims, 1 Drawing Sheet

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 52 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:1:

TTCAACATCA GTGAAAATCT TTTTTAACC GGTCAAACCG AATAAGGAGC CT          52

( 2 ) INFORMATION FOR SEQ ID NO:2:

( i ) SEQUENCE CHARACTERISTICS:
      ( A ) LENGTH: 51 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:2:

TTCAACATCA GTGAAAATCT TTTTTAACC GGTCAAACCG AATAAGGAGC C           51

FLUORESCENT POLYMER LABELED CONJUGATES AND INTERMEDIATES

This application is a continuation-in-part of U.S. patent application Ser. No. 08/270,285, filed Jul. 11, 1994, abandoned, which is a continuation-in-part of U.S. patent application Ser. No. 08/091,149, filed Jul. 13, 1993, abandoned.

TECHNICAL FIELD

The present invention relates to a fluorescent conjugate which is useful in specific binding assays. More particularly, the invention relates to compositions and intermediates for a highly-fluorescent water-soluble conjugate which comprises a specific binding member linked to a highly fluorescent polymer.

BACKGROUND OF THE INVENTION

The affinity for binding displayed by antibodies towards cell surfaces is often exploited as the basis for imaging systems used for cytometric and/or hemotologic analysis of cell samples (hereinafter test samples). Imaging systems often employ antibodies as binding molecules which specifically bind sites on the surfaces of specific cells contained in a test sample. In order to detect whether the antibody has bound to the surface of a cell, it is tagged or labeled with a fluorescent molecule. The antibody and its fluorescent molecule are collectively referred to as a conjugate.

In a typical cytometric or hemotologic analysis, the conjugate is contacted with a test sample, which is usually blood or a fraction thereof which contains a variety of cell populations, to form a test mixture. The mixture is incubated for a time and under conditions sufficient for the conjugate to bind target sites on the surface of certain cell populations. After the incubation period, an energy source excites the fluorescent molecule of the conjugate, thereby causing it to fluoresce. This fluorescence is detected using, for instance, a camera that detects cell images via the fluorescence of the bound conjugate. Cameras currently used in imaging systems are highly sensitive and as a result, are very expensive. These cameras are necessarily sensitive because they must detect conjugates that have a relatively low fluorescence. For example, the conjugates currently used in imaging systems typically have a Molecules of Equivalent Soluble Fluorochrome (MESF) value of approximately 12,000. A fluorescently stained cell having a MESF value of 12,000 can reliably be imaged by a photometric cooled Charged-Coupled Device (CCD) camera with 12 bits, 4,096 levels and 500×386 pixels. This type of camera costs approximately 20,000 dollars and is a major cost associated with the production of an imaging system.

There have been several attempts to produce a conjugate which has a MESF value that is detectable by a less sensitive and thereby less expensive camera. Previous attempts to enhance the fluorescence of conjugates have sacrificed the conjugates binding efficiency for a brighter conjugate. For example, in an attempt to increase the fluorescence of a conjugate, antibody has been randomly labeled with multiple fluorescent molecules (sometimes referred to as fluorophores). While this random labeling increases the number of fluorophores per antibody, it also binds fluorophores to the binding region of the antibody. When this region is thus bound by a fluorophore, it is incapable of binding its target and thus cannot image cell surfaces and serve its intended purpose. In addition, labeling an antibody with multiple fluorophores often leaves the Fc portion of the antibody unhindered and capable of binding Fc receptors which may be present on the surface of cells contained in a test sample. Because of their ability to bind in this manner, non-specific binding of the conjugate occurs and misleading images are the result.

In another attempt to increase the fluorescence of imaging conjugates, multiple fluorophores have been attached to a polymer and the polymer was attached to an antibody. However, this conjugate does not serve its intended purpose because it suffers significant quenching, and therefore, signal loss caused by the inadequate spacing between multiple fluorophores on a polymeric backbone that has a limited amount of space.

In yet another attempt to increase the fluorescence of imaging conjugates, fluorescent microparticles or colloidal particles have been attached to an antibody thereby increasing the fluorescence of the conjugate. However, this type of conjugate suffers the malady of being insoluble. Because these conjugates are insoluble, they are recognized as foreign bodies by phagocytes that are often present in test samples. As a result, these conjugates are ingested by the phagocytes and the fluorescence associated with such a cell is due to the fluorescent particle in the phagocyte, not the result of a conjugate bound to a marker on the surface of a cell.

Molecules known as cyclodextrins have been used in the art of conjugate synthesis. Cyclodextrin is a well known water soluble cyclic oligosaccharide having a hydrophobic center cavity and a hydrophilic outer region. Generally, the shape of a cyclodextrin molecule is cylindrical with one end of the cylinder having a larger opening than the other. The larger opening is known as the secondary rim and the other opening is known as the primary rim. A cavity into which small molecules can enter through the larger secondary rim is present between the two openings of the cyclodextrin molecule and, in aqueous systems, the cavity of a cyclodextrin molecule (the "host") provides a hydrophobic microenvironment for the complexing of small molecular weight hydrophobic molecules (the "guest").

Efforts to generate polymeric cyclodextrin have also been made in an attempt to increase the fluorescence associated with conjugates. Theoretically, the complexing properties of a single cyclodextrin molecule can be magnified by having several cyclodextrin molecules in close proximity to each other (i.e. having several cyclodextrin molecules in close proximity to each other increases the probability that a guest molecule will enter the cavity of a cyclodextrin molecule). Thus, as the theory goes, if a polymeric cyclodextrin molecule were created, it would be capable of hosting a plurality of guest molecules. Further, if the guest molecules of a polymeric cyclodextrin molecule were signal generating groups, there would be several, for instance, fluorophores in close proximity to each other and the fluorescence associated with the polymer would be greater than that of a single fluorophore. Hence, if a conjugate were made with a fluorophore containing polymeric cyclodextrin its fluorescence would, theoretically, be greater than a conjugate made with a single fluorophore.

Several cyclodextrin based polymers have been manufactured to validate the above mentioned theory. However, these polymers suffer from problems that severely limit their desired effect. These cyclodextrin based polymers are synthesized using cyclodextrin monomers that have been modified to contain several reactive groups on the cyclodextrin's primary and secondary rims which allows these monomers to react via their primary and secondary rims, and react multiple times via their multiple reactive groups. When a cyclodextrin molecule is bound by its secondary rim, the larger opening to the hydrophobic cavity is hindered. As a result, it is difficult for a guest molecule to enter the cavity of the cyclodextrin, and the cyclodextrins utility as a host is sacrificed. Further, forming polymers with cyclodextrins having multiple reactive groups, allows a high degree of crosslinking. When crosslinking occurs not only are the cyclodextrins bound by the secondary rim, causing the problems mentioned above, but a matrix of cyclodextrins forms. Consequently, the number of cyclodextrins polymerized is limited and many of the cyclodextrins polymerized get buried within the matrix. Although many cyclodextrins are in close proximity, very few of them have accessible secondary openings and very few guest/host complexes are able to form. The problems associated with the above polymers stem from their methods of production. Specifically, the monomeric cyclodextrins employed to synthesize the polymers are over-reactive.

In order to synthesize a useful polymeric cyclodextrin it is necessary to have a properly reactive monomeric cyclodextrin building block. An example of such a reactive cyclodextrin is 6-cyclodextrin monoaldehyde. Previous routes to 6-cyclodextrin monoaldehyde have been described, but these synthetic procedures require multiple steps which include the synthesis of toxic and potentially explosive intermediates. Additionally, these procedures require materials that are hard-to-obtain and expensive. Thus, in order to effectively use the complexing properties of cyclodextrin, particularly in relation to conjugate synthesis, a safer and more efficient route to 6-cyclodextrin monoaldehyde is needed.

Reducing the expense of imaging systems can be accomplished by reducing the cost of one of its most expensive components. Specifically, if a low cost camera were able to be used in an imaging system the cost of the entire system would be greatly reduced. Given the present state of imaging conjugate technology this is not practical. There is therefore a need for a conjugate capable of emitting a signal capable of detection by a low cost camera.

SUMMARY OF THE INVENTION

In accordance with the present invention there is provided a conjugate which emits an amount of fluorescence that is detectable by a detection device which has a relatively low degree of sensitivity. Additionally, intermediates and novel methods useful for synthesizing the intermediates are provided. The conjugate of the present invention can be employed in essentially any application which utilizes a fluorescent entity immobilized on a specific binding member.

The conjugate herein provided comprises a specific binding member which is covalently bound to at least one highly fluorescent polymer. The highly fluorescent polymer comprises a backbone polymer which has fluorescent compounds directly bound thereon. Alternatively, the backbone polymer can have cyclodextrin molecules covalently attached thereon and the fluorescent compounds can be hosted within the hydrophobic microenvironments of the cyclodextrin molecules, thereby indirectly associating the signal generating groups with the polymer. When the fluorescent compounds are directly bound to the backbone polymer, cyclodextrin molecules can be added to the polymer indirectly by having them associate with the bound signal generating groups, or cyclodextrin can be added to the fluorescent polymer by covalently binding cyclodextrin thereon.

According to another feature of the invention, there is provided a process for creating 6-cyclodextrin monoaldehyde. The process herein provided allows site specific introduction of an aldehyde group to a cyclodextrin molecule. The process introduces a single aldehyde group to the primary rim of a cyclodextrin molecule thereby creating a reactive cyclodextrin molecule that, when reacted, does not crosslink and avoids hindering the opening of the larger secondary rim.

The process for preparing 6-cyclodextrin monoaldehyde comprises the steps of:

a) converting a cyclodextrin molecule of the formula

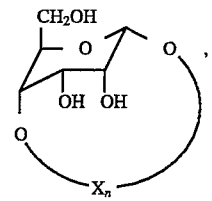

wherein X is

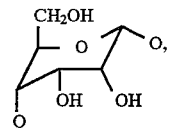

and n is 5, 6, or 7, to its monotosylate derivative of the formula

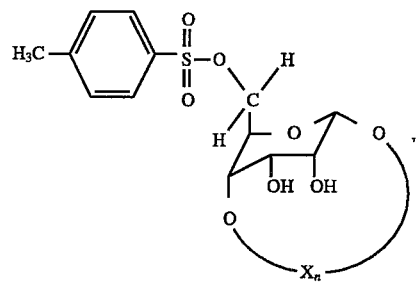

wherein X and n are defined as above; and b) converting the monotosylate derivative of step (a) to 6-cyclodextrin monoaldehyde of the formula

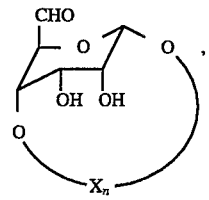

wherein X and n are defined as above.

DETAILED DESCRIPTION OF THE INVENTION

Figure 1:
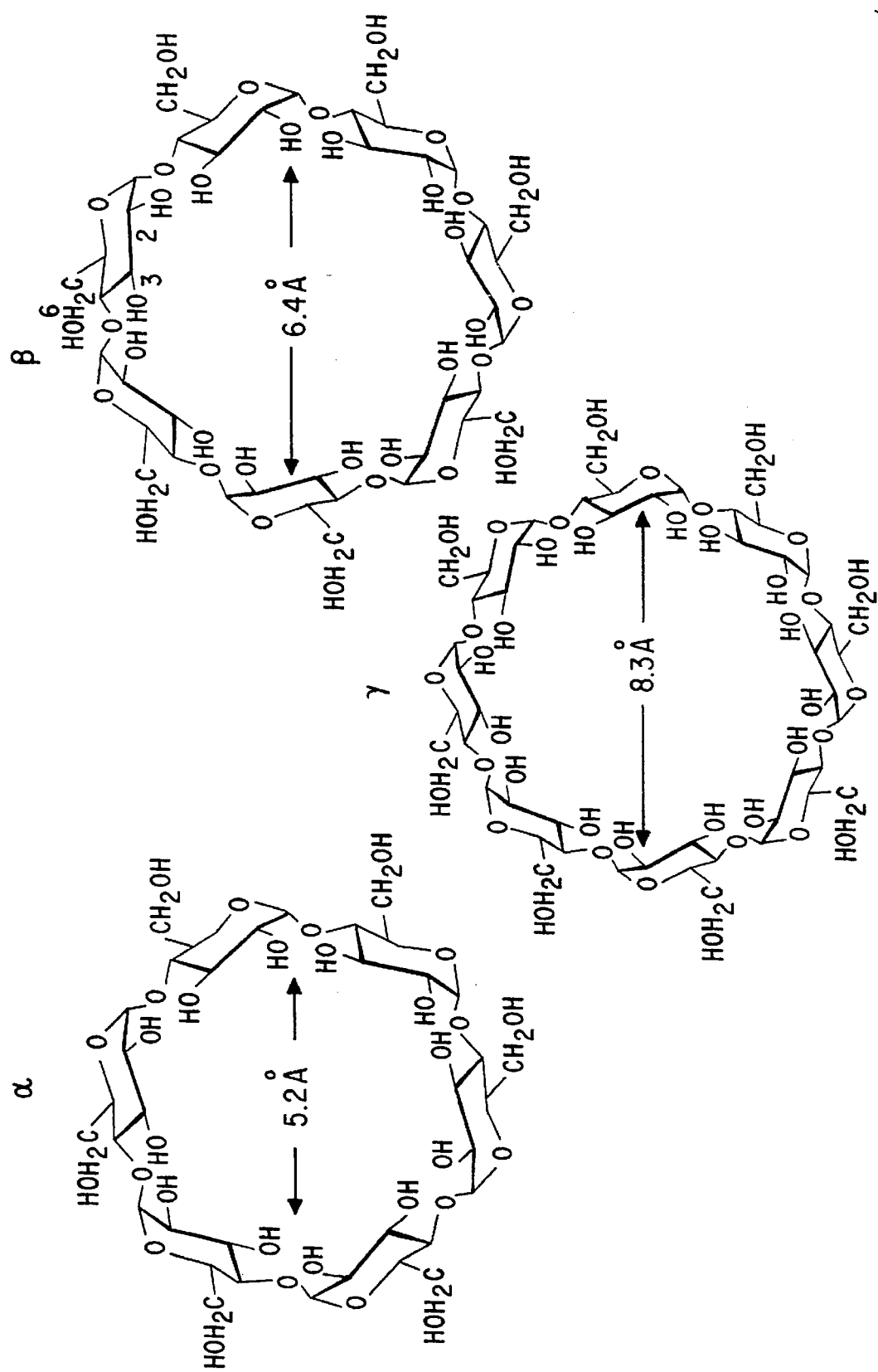
FIG. 1 shows alpha ($\alpha$), beta ($\beta$) and gamma ($\gamma$) cyclodextrin and the system for numbering the glucose units therein.

The following definitions are applicable to the invention:
Definitions

The term "analyte", as used herein, refers to the compound or composition to be detected or measured and which has at least one epitope or binding site. The analyte can be any substance for which there exists a naturally occurring binding member or for which a binding member can be prepared. Analytes include, but are not intended to be limited to, toxins, organic compounds, proteins, peptides, microorganisms, amino acids, carbohydrates, nucleic acid sequences, hormones, steroids, vitamins, drugs (including those administered for therapeutic purposes as well as those administered for illicit purposes), virus particles and metabolites of or antibodies to any of the above substances. For example, such analytes include, but are not intended to be limited to, RNA; DNA; ferritin; creatinine kinase (CK-MB); digoxin; phenytoin; phenobarbitol; carbamazepine; vancomycin; gentamycin; theophylline; valproic acid; quinidine; leutinizing hormone (LH); follicle stimulating hormone (FSH); estradiol; progesterone; IgE antibodies; vitamin B2 micro-globulin; glycated hemoglobin (Gly Hb); cortisol; digitoxin; N-acetylprocainamide (NAPA); procainamide; antibodies to rubella, such as rubella-IgG and rubella-IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti hepatitis B core antigen IgG and IgM (Anti-HBC); human immune deficiency virus 1 and 2 (HTLV); hepatitis B e antigen (HBeAg); antibodies to hepatitis B e antigen (Anti-HBe); thyroid stimulating hormone (TSH); thyroxine (T4); total triiodothyronine (Total T3); free triiodothyronine (Free T3); carcinoembryoic antigen (CEA); alpha fetal protein (AFP); and drugs of abuse and controlled substances, including but not intended to be limited to, amphetamine; methamphetamine; barbiturates such as amobarbital, secobarbital, pentobarbital, phenobarbital, and barbital; benzodiazepines such as librium and valium; cannabinoids such as hashish and marijuana; cocaine; fentanyl; LSD; methapualone; opiates such as heroin, morphine, codeine, hydromorphone, hydrocodone, methadone, oxycodone, oxymorphone and opium; phencyclidine; propoxyhene; and the like. The term "analyte" also includes any antigenic substances, haptens, antibodies, macromolecules and combinations thereof. Further, the term "analyte" also includes the product or products of a nucleic acid amplification reaction, variably known as an "amplicon", which can be labeled with haptens recognizable by specific binding members.

The term "cyclodextrin" as used herein refers to α, β or γ cyclodextrin.

The term "optimized highly-fluorescent-polymer" as used herein refers to a polymer which has multiple signal generating groups immobilized thereon. The immobilized signal generating groups are spaced along the polymer in such a manner as to maximize the signal generated from the signal generating groups and to minieffect as quenching effect associated with having multiple signal generating groups too close to each other.

The term "primary reagent" as used herein refers to an agent which specifically binds an analyte and is used as a bridge between the analyte, to which it is bound, and a conjugate which binds the primary reagent.

The term "signal generating group" as used herein refers to a fluorescent compound (sometimes referred to as a fluorophore) which is capable of absorbing energy and emitting light or fluorescing. Examples of signal generating groups include, but are not intended to be limited to fluorescein, cascade blue, Texas Red™, p-phthalocyanines, cyanine dyes, thiazoles, dansyl, napthalene, p-tohidinyl napthalene sulfonic acid, coumarin, phycoerythrin, allophycocyanine and the like.

"Specific binding member", as used herein, means a member of a specific binding pair, i.e., two different molecules where one of the molecules through chemical or physical means specifically binds to the other molecule. In addition to antigen and antibody specific binding pairs, other specific binding pairs include, but are not limited to, avidin and biotin, carbohydrates and lectins, complementary nucleotide sequences, complementary peptide sequences, effector and receptor molecules, an enzyme cofactor or substrate and an enzyme, an enzyme inhibitor and an enzyme, polymeric acids and bases, dyes and protein binders, peptides and specific protein binders (e.g., ribonuclease, S-peptide and ribonuclease S-protein),and the like. Furthermore, binding pairs can include members that are analogs of the original binding member, for example, an analyte-analog or a binding member made by recombinant techniques or molecular engineering. If the binding member is an immunoreactant it can be, for example, a monoclonal or polyclonal antibody, a recombinant protein or recombinant antibody, a chimeric antibody, a mixture(s) or fragment(s) of the foregoing.

The term "test sample", as used herein, refers to a material suspected of containing analytes. The test sample can be used directly as obtained from the source or following a pretreatment to modify the character of the sample. The test sample can be derived from any biological source, such as a physiological fluid, including, blood, saliva, ocular lens fluid, cerebral spinal fluid, sweat, urine, milk, ascites fluid, mucous, synovial fluid, peritoneal fluid, amniotic fluid and the like, and fermentation broths cell cultures, and chemical reaction mixtures and the like. In addition to biological or physiological fluids, other liquid samples can be used such as water, food products and the like for the performance of environmental or food production assays. In addition, a solid material suspected of containing an analyte can be used as the test sample. In some instances, it may be beneficial to modify a solid test sample to form a liquid medium or to release an analyte. The test sample can be pretreated prior to use by, for example, preparing plasma from blood, diluting viscous fluids, filtering liquids, distilling liquids, concentrating liquids, inactivating interfering components, adding reagents, and the like.

According to the present invention, the water soluble backbone polymer used for production of the conjugate herein provided comprises an amine functional polymer that is typically amine functional with the following amine functional groups:

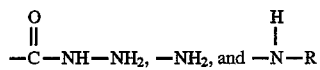

wherein R is selected from the group consisting of $C_1$-$C_3$ alkyl, isopropyl, —$(CH_2)_2CO_2^-$, —$(CH_2)_2SO_3^-$, —$(CH_2)_2NH_3^+$, —$(CH_2)_2NH_2^+(CH_2)_2SO_3^-$, —$(CH_2)_2O(CH_2)_2O(CH_2)_2OH$ and —$(CHOH)_4CH_2OH$. The amine functional polymer may also have combinations of the above listed amine functionalities. Preferably the polymer has an average molecular weight of between about 20,000 and 300,000, more preferably between about 100,000 and 250,000, and most preferably between about 150,000 and about 200,000.

When signal generating groups are to be directly bound to the backbone polymer, the signal generating groups preferably have a reactive group that is suitable for forming covalent bonds with the amine functional polymer. Signal generating groups that are capable of such a reaction include, but are not limited to those having succinimidyl active esters, acid halides, sulfonyl halides, aldehydes, iodoacetyls, or maleimido groups. Examples of signal generating groups that may carry the aforementioned functionalities include, fluorescein, cascade blue, Texas Red™, p-phthallocyanines, cyanine dyes, thiazoles, dansyl, napthalene, p-toluidinyl napthalene sulfonic acid, coumarin, phyeoerythrin, allophycocyanine and the like.

As previously mentioned, the signal generating groups can be non-covalently hosted within a hydrophobic cavity of a cyclodextrin molecule that is coralenity bound to the polymer backbone. In this situation the signal generating groups do not need to carry any reactive group. However, as it will be understood by one skilled in the art, the signal generating group will be one that is capable of being hosted by the particular cyclodextrin molecule being used.

As previously stated, signal quenching is caused when multiple dyes are randomly placed on a single polymer. This quenching is substantially reduced through optimization of the number of dyes associated with a single backbone polymer. By optimizing the number of dyes placed on a single backbone polymer, the individual dyes are not as susceptible to quenching. Through optimization of the signal generating groups on the backbone polymer, the conjugate of the instant invention is able to emit a signal that can be detected by a detection device that has a relatively low sensitivity and is relatively inexpensive. Further, by mixing monomeric cyclodextrin, under appropriated conditions, with a preparation of optimized fluorescent polymer conjugate, the signal emitted by the polymer is enhanced even further. It has been surprisingly and unexpectedly discovered that the signal generated by the conjugate of the instant invention can be increased up to approximately 35 times over that of the conjugates presently available.

The fluorescent polymer can be bound to any specific binding member that is reactive with an amine functional group present on the backbone polymer. Although many specific binding members are suitable for use in the conjugate of the instant invention, antibodies are preferred.

The conjugate of the instant invention can be used in a variety of applications which utilize fluorescence to detect a specific binding event. Such applications include, but are not limited to image analysis, flow cytometry, immunoassays, fluorescent cell staining, fluorescent microscopy and the like.

Binding signal generating groups to a backbone polymer can be accomplished by reacting the amine groups which are present on the backbone polymer with the reactive groups present on the signal generating groups. This process of binding the signal generating groups to the polymer is referred to as loading the polymer. However, merely loading a polymer with signal generating groups may not result in a polymer which emits the greatest amount of fluorescence achievable. This can be the result of overloading a polymer which results in quenching, or under loading a polymer that could accommodate more signal generating groups without experiencing quenching. Thus, it is preferred that the number of signal generating groups loaded on a polymer be optimized in order to generate a polymer capable of emitting the greatest amount of signal.

Optimizing the number of fluorophores on an amine functional polymer can be accomplished by executing a series of optimization loadings and then determining which loading yields the polymer which emits the greatest amount of signal. Generally, this procedure can be executed by creating a panel of trial loadings which combine varying concentrations of signal generating groups with a constant amount of polymer. The loaded polymers can then be purified from any unreacted compounds by a variety of methodologies well known to those of ordinary skill in the art, such as precipitation, isoelectric focussing or, preferably, size exclusion chromatography. The purified polymers can then be tested for their ability to emit a signal to determine which loading concentration yields the polymer which emits the greatest amount of signal. Typically, the polymer displaying the greatest amount of signal has been optimally loaded and the concentration it was loaded at can be used to optimally load preparative amounts of the fluorescent polymer.

The preferred method for optimizing the number of signal generating groups on a particular polymer can be accomplished by first calculating the molecular weight of the desired water soluble polymer and determining the total molar quantity of amine functional groups present on the polymer. Next, a panel, consisting of a series of solutions each of which contains a different concentration of signal generating group, is created. The panel solutions comprise varying concentrations of the signal generating group dissolved in a suitable solvent, for example, dimethylformamide (DMF) or dimethylsulfoxide (DMSO). The various concentrations are based on the total molar amount of amine functionality present on the amine functional polymer and a typical panel can include the following concentrations: 5%, 10%, 15%, 20%, 40%, 75%, 100%, 140% and 200% of the total molar quantity of amine functional groups present on the chosen polymer. The panel concentrations are preferably carried out far enough so that quenching will occur, thereby clearly delineating the point at which the polymer is optimally loaded. After the panel has been set up, each panel member is added to individual and equimolar solutions of the polymer.

Each solution of loaded polymer can then be purified from unreacted polymer and/or signal generating groups using techniques well known in the art. As previously mentioned, after the polymers are purified they can be analyzed for their ability to emit signal and a preparative amount of polymer can then be produced using the data so obtained. Alternatively, further optimization panels can be executed to more accurately determine the optimal loading concentration. It is to be understood, of course, that the manner by which a polymer is optimized is not intended to be limited to the methods described herein, and that other methods can be employed as well.

The highly fluorescent polymer can be attached to a specific binding pair member using a variety of techniques well known in the art. It is a preferred feature of this invention to covalently bond the fluorescent polymer or polymers at or near the Fc portion of an antibody. Attaching the polymer to an antibody in this manner sterically hinders the Fc portion of the antibody thereby preventing it from binding, for example, Fc receptors present on the surface of certain cell populations. Additionally the site specific attachment leaves the hypervariable regions of the antibodies unhindered and capable of binding their intended target. It is to be understood, of course, that the manner by which a specific binding member is attached to a fluorescent polymer is not intended to be limited to the methods described herein, and that other methods well known in the art can be employed as well.

A fluorescent polymer can be attached to an antibody by oxidizing the Fc region of the antibody and then reacting the oxidized antibody with a polymer of the type described herein. The antibody is preferably oxidized at a concentration of between about 1.0 mg/ml and about 20.0 mg/ml, more preferably between about 1.0 mg/ml and about 10.0 mg/ml, and most preferably between about 2.0 mg/ml and about 5.0 mg/ml. If the antibody is obtained in concentrations outside of these ranges, it can be concentrated by means well known to those of ordinary skill in the art or diluted with an appropriate buffer. The antibody is preferably oxidized in a suitable buffer having a pH between about 6.5 and about 8.0, more preferably between about 7.0 and about 8.0, and most preferably between about 7.5 and about 8.0. The oxidation of the Fc region of the antibody can be effectuated using an oxidizing agent well known to those skilled in the art. Such oxidizing agents include, but are not limited to sodium periodate, chromium dioxide, potassium permanganate, manganese dioxide, bromine, and the like. The oxidizing agent solution typically has a concentration of between about 100 mM and about 250 mM, preferably between about 150 mM and about 200 mM, and most preferably between about 175 mM and about 200 mM. The oxidation of the antibody can take place at a temperature of between about 2° C. and about 30° C., preferably the oxidation takes place a temperature between about 2° C. and about 8° C. for approximately between 15 minutes and about 5 hours, preferably between about 1 hour and 2 hours. After the antibody has been oxidized it can be purified, by methods well known in the art, and placed in an appropriate buffer having a pH in the range of about 3 and about 6, preferably in the range of about 4 and about 5. The oxidized antibody is then ready to be coupled to the fluorescent polymer. It is to be understood, of course, that the manner by which an antibody is oxidized is not intended to be limited to the methods described herein, and that other methods well known in the art can be employed as well.

When reacting, for example, an oxidized antibody with a fluorescent polymer, the concentration of the polymer can be in the range of about 1.0 mg/ml and about 20.0 mg/ml, preferably in the range of about 2.0 mg/ml and about 5.0 mg/ml in an appropriate buffer having a pH in the range of about 4.0 and about 7.0, preferably in the range of about 4.0 and about 5.0. Although many buffers are suitable, the preferred buffer is a sodium acetate buffer having between about 50 mM and 200 mM sodium acetate, and between about 75 mM and 150 mM sodium chloride. The amount of polymer added to the oxidized antibody can be in the range of about 1.0 and about 20 equivalents of polymer to antibody based on the molecular weight of the antibody and the estimated molecular weight of the fluorescent polymer. The reaction between the oxidized antibody and the fluorescent polymer can take place at a temperature between about 2° C. and about 30° C., preferably between about 2° C. and about 8° C. in a light tight container. The reaction can be allowed to run for between about 2 and about 48 hours, preferably between about 12 and about 15 hours. Upon completion of the reaction the conjugate can be purified from the unreacted components of the reaction mixture using purification methodologies known to those skilled in the art.

In cases where primary or secondary amine functional fluorescent polymers are covalently bound to a specific binding member, an additional step is preferred. Specifically, as a result of the initial reaction between the antibody and polymer, a Schiff Base is formed and the reduction of the Schiff Base can be accomplished by methods well known in the art such as the use of a suitable reducing agent such as $NaCNBH_3$ at a concentration in the range of between about 0.25 mg/ml and 2.0 mg/ml. The reduced conjugate can then be purified from excess reactants using purification techniques well known in the art and mentioned above. It is to be understood, of course, that the manner by which a Schiff Base is reduced is not intended to be limited to the methods described herein, and that other methods can be employed as well.

As previously mentioned, cyclodextrin can be used to enhance the fluorescence of the conjugate provided herein. One way in which the fluorescence of the conjugate can be enhanced is by adding cyclodextrin to an assembled conjugate (i.e. a specific binding member covalently bound to a highly fluorescent polymer). Cyclodextrin used in this manner does not require that any modification be made to the cyclodextrin molecule or the conjugate. Although the exact mode of association is not known, it is believed that the cyclodextrin associates with the signal generating groups present on the polymer backbone by hosting the bound signal generating groups within the hydrophobic center of the cyclodextrin molecule. When cyclodextrin is used in this manner, it is preferably used in concentrations in the range of between about 5 mM and 200 mM, preferably in the range of between about 10 mM and 20 mM.

Enhancement of the signal generated by the conjugate herein described may also be achieved by directly binding cyclodextrin to the conjugate's polymer backbone. The cyclodextrin can be covalently attached to the polymer backbone to which signal generating groups are covalently bound, or covalently attached to the backbone polymer by itself. In the latter situation the signal generating groups can become associated with the fluorescent polymer via a guest/host relationship with the covalently bound polymeric cyclodextrin molecules. After this relationship has occurred, the polymer can be purified from the remaining unhosted signal generating groups by methods well known in art. In order to allow this guest-host relationship to occur, the cyclodextrin molecule should be bound in such a manner that allows the secondary rim of the cyclodextrin molecule to remain unhindered and therefore open to receive a signal generating group into the hydrophobic cavity.

By selectively adding a single reactive group to the primary rim of the cyclodextrin molecule the cyclodextrin molecule can be bound to the backbone polymer by its primary rim. Thus, the secondary rim will be unhindered and the hydrophobic cavity will be accessible to guest molecules.

Covalently binding the primary rim of a cyclodextrin molecule to an amine functional polymer can be accomplished by adding a single aldehyde group to the primary rim of the cyclodextrin molecule. Once the single aldehyde is added to the cyclodextrin molecule it can be directly reacted With an amine group present on the amine functional polymer whereby the cyclodextrin is attached to the polymer via a single covalent bond to the cyclodextrin's primary rim. Thus, the cyclodextrin is bonded to the polymer in such a way as to leave the secondary rim unhindered and therefore accessible to guest molecules.

As previously mentioned, the addition of a single aldehyde group to the primary rim of a cyclodextrin molecule can be accomplished using methodologies known in the art. However, these methods involve the production of intermediates that are potentially dangerous. For example, an aldehyde can be added to the primary rim of cyclodextrin using the Dess-Martin periodonane reagent. D. B. Dess et al., *J. Org. Chem.*, 48, 4155–4156 (1983). This reaction can be carried out in a heterogeneous system containing a stoichiometric amounts of Dess-Martin reagent and cyclodextrin dissolved in tetrahydrofuran (THF). Although, 6-cyclodextrin monoaldehyde is produced, Dess-Martin reagent is potentially explosive and is no longer readily available from a commercial source. Other routes to the monoaldehyde involve three to four steps that produce toxic and potentially explosive azide intermediates.

Alternatively, a method of producing 6-cyclodextrin monoaldehydes has been discovered that does not involve the production of dangerous intermediates and is carried out using materials that are readily available commercially. Generally, the method is a two step process that can be carried out as shown below in Scheme I.

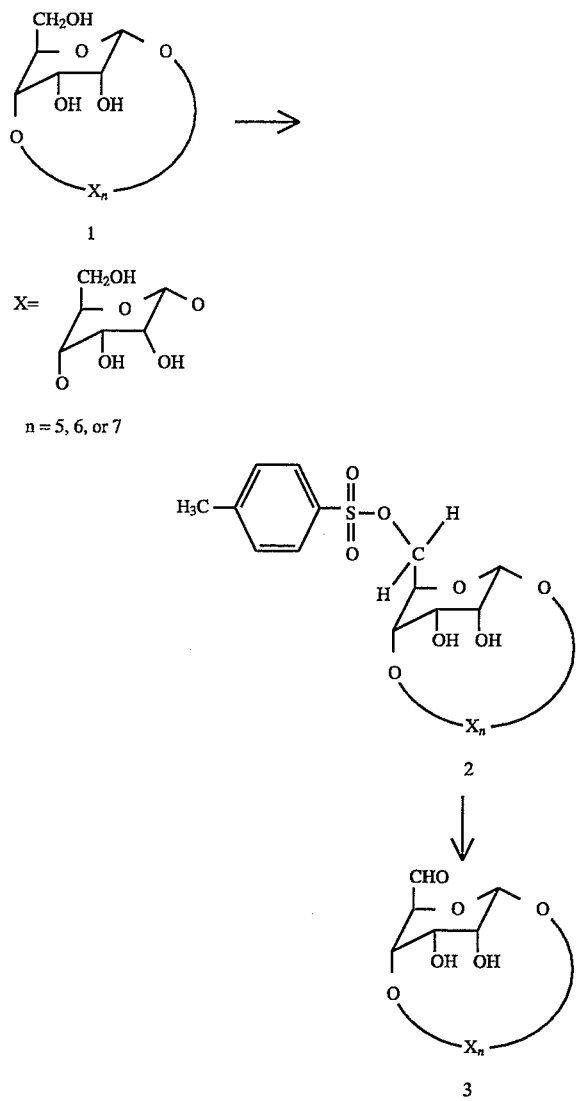

The first step of the method is to convert a cyclodextrin of the formula 1 to its monotosylate derivative of the formula 2. The tosylate derivative of formula 2 is then oxidized to yield the cyclodextrin monoaldehyde of the formula 3.

There are several acceptable methods of converting the cyclodextrin of the formula 1 to its monotosylate derivative of the formula 2. See L. D. Melton et al., *Carbohyd. Res.*, 18, 29–37 (1971) or R. C. Petter et al., *J. Am. Chem. Soc.* 112, 3360–3868 (1990). After the monotosylate of the formula 2 has been formed, it can be purified from the reaction mixture using methodologies well known to those skilled in the art, preferably, High Performance Liquid Chromotography (HPLC). The solid monotosylate can then be recovered by drying the solvent from the dissolved cyclodextrin mono-tosylate using methods well known to those skilled in the art. The solid cyclodextrin monoaldehyde is then ready for use in the second step of the process.

The second oxidative step of the conversion can be achieved using multiple methods. Generally the oxidation step is a dimethylsulfoxide (DMSO) mediated reaction that can be catalyzed through the addition of a base. It was found that heating the monotosylate derivative between about 75° C. and about 85° C. in DMSO resulted in the slow conversion (about 1–3 days) of the tosylate derivative to the monoaldehyde of the formula 3.

The addition of base to the DMSO mediated reaction accelerates the rate of conversion from the monotosylate to the monoaldehyde of the formula 3. For example, a trace amount of NaOH accelerated the reaction. Preferred bases for use in this step of the process include hindered amine bases such as diisopropyl amime, N-methyl morpholine, triethyl amine, trimethyl amine and the like. Diisopropylethyl amine (a.k.a. Hunig's Base) is a particularly preferred hindered amine base. Preferably the conversion of the monotosylate to the monoaldehyde is accomplished when the monotosylate is in solution at a concentration of between about 0.5% (w/v) and about 20% (w/v), more preferably between about 1% (w/v) and about 15% (w/v), and most preferably between about 2% (w/v) and about 10% (w/v). The amount of hindered amine base used for the conversion can be between about 0.1 and about 1.0 molar equivalents of the monotosylate in solution, preferably between about 0.3 and about 0.7 molar equivalents of the monotosylate in solution. The cyclodextrin monoaldehyde thusly formed can be purified from any unreacted material using methods well known in the art and reacted with an amine functional polymer or the final reaction mixture can be directly reacted with an amine functional polymer.

Using standard covalent chemistry methods well known to those skilled in the art, the cyclodextrin monoaldehyde provided herein is easily attached to compounds that have amine functionalities. Examples of such amine functionalities include, but are not intended to be limited to

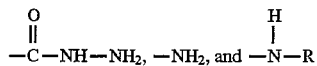

wherein R is selected from the group consisting of; $C_1$–$C_3$ alkyl, isopropyl, —$(CH_2)_2CO_2^-$, —$(CH_2)_2SO_3^-$, —$(CH_2)_2NH_3^+$, —$(CH_2)_2NH_2^+(CH_2)_2SO_3^-$, —$(CH_2)_2O(CH_2)_2O(CH_2)_2OH$ and —$(CHOH)_4CH_2OH$. Examples of compounds that are amine functional with these groups include amine functional polymers such as polyacrylamide hydrazide or amine functional solid phases such as aminated microparticles.

In cases where primary or secondary amine functional compounds are covalently reacted with cyclodextrin monoaldehyde, an additional step is preferred. Specifically, after the initial reaction between the compound and the monoaldehyde takes place, a Schiff Base is formed and the reduction of the Schiff Base can be accomplished in the manner previously described.

The cyclodextrin monoaldehyde can be attached to amine functional polymers or amine functional polymers which are optimally loaded with signal generating groups. If the cyclodextrin monoaldehyde is added to an amine functional polymer, the polycyclodextrin polymer can subsequently be rendered fluorescent with signal generating groups. One way in which the polycyclodextrin polymer can be rendered fluorescent is through the covalent attachment of the signal generating groups to the amine functional polymer. If the polymer is rendered fluorescent in this manner, it will be understood that some of the amine functional groups of the polymer must be available for reaction.

Another way in which the polycyclodextrin may be rendered fluorescent is by adding signal generating groups to a solution containing the polycyclodextrin polymer or a solution containing the polycyclodextrin bound to a specific binding member. When using this method of derivatization, the hosting ability of the cyclodextrin is exploited as outlined above. In addition, after the hosting ability has been exploited, excess signal generating groups can be removed as outlined above.

After a polycyclodextrin/polysignal generating group polymer is produced it can then be attached to a specific binding member as outlined above.

As previously mentioned the completed conjugate has a variety of uses. The preferred method of using the conjugate of the instant invention is in a flow cytometry application which employs a fluorescent conjugate or multiple fluorescent conjugates to detect cells contained in a test sample. An example of a flow cytometer includes the Fluorescence Activated Cell Sorter (FACS II) manufactured by Becton, Dickinson & Co, Franklin Lakes, N.J. In general, an imaging system contains an excitation source and a detection device. The excitation source excites the signal generating group associated with the conjugate and the detection device detects the signal emitted from the excited signal generating group.

In a typical imaging system analysis, a test sample is incubated with a fluorescent conjugate which specifically binds certain cells that may be present in the test sample. The incubation takes place for a time and at a temperature conducive for the binding of the conjugate to specific cell populations contained in the sample. The cells bound with the conjugate are commonly referred to as being stained and the staining procedure can be executed multiple times, sequentially or at the same time, with multiple conjugates which emit signals of varying wavelengths. After the staining procedure is complete, the sample can be analyzed using a flow cytometer.

In an alternative preferred embodiment of the present invention, a test sample is incubated with a solution of primary reagent which specifically binds certain cells that may be present in the test sample to form primary complexes. The unbound reagent, if any, can be washed from the sample and a fluorescent conjugate specific for the bound primary reagent is then incubated with the primary complexes. The unbound conjugate, if any, can then be removed from the primary complexes and the fluorescence associated with the cells can then be determined as above. It will be understood that the staining procedure can be repeated multiple times with primary reagents specific for different cell markers and conjugates which fluoresce at the same or at different wavelengths. It will also be understood, of course, that the staining procedure can be accomplished in a sequential manner or in a batch type manner wherein all of the components necessary for cell staining are added to the sample before the fluorescence associated with the cells is determined.

In an another alternative embodiment, the conjugate and method of the present invention can be adapted for use in conventional solid phase immunoassays such as, for example, a sandwich assay. A sandwich type immunoassay typically involves contacting a test sample suspected of containing an analyte with a substantially solid inert plastic, latex or glass bead or microparticle, or other support material which has been coated with a specific binding member which forms a binding pair with the analyte. The binding member coated support material is commonly referred to as a "capture reagent". After the analyte is bound to the support material the remaining test sample is removed from the support and the analyte bound support material is treated with a conjugate which generally comprises a second binding member labeled with a signal generating group. The conjugate becomes bound to the analyte which is bound on the support and the solid support, having the first binding member, the analyte and conjugate bound thereon is separated from any unbound conjugate, typically with one or more wash steps. The signal generated by the signal generating group, through appropriate excitation, can then be observed visually, or more preferably by an instrument, to indicate the presence or amount of an analyte in a test sample. It will be understood, of course, that the order and number of the steps employed to perform such assays are not intended to limit the invention herein provided.

As previously mentioned, the analyte detected by such an immunoassay can be the product or products of an amplification reaction. Accordingly, the analytes can comprise nucleic acid sequences or are otherwise the products of a hybridization reaction such as LCR which is described in European Patent Applications EP-A-320-308 and EP-A-439-182 and PCR which is described in U.S. Pat. Nos. 4,683,202 and 4,683,195 all of which are herein incorporated by reference. In cases where the analytes comprise, for example, LCR or PCR reaction products or sequences, the sequences can comprise or be modified to comprise a binding member that forms a binding pair with an indicator reagent and a binding member which forms a binding pair with a capture reagent.

Automated systems suitable for performing sandwich type assays such as, for example, a Microparticle Enzyme ImmunoAssays (MEIAs) are well known in the art. A particularly preferred and commercially available automated instrument which can be employed to perform the method herein provided is the IMx® system which is available from Abbott Laboratories, Abbott Park, Ill. Protocols for MEIAs such as those performed by the Abbott IMx® instrument are well known in the art and have been described in Fiore, M. et al., *Clin. Chem.*, 34/9:1726–1732 (1988). An exemplary protocol is as follows. 100 µl of a test sample is pipetted into the sample well of an IMx® reaction cell. 30–50 µl of the sample and an anti-analyte coated microparticle suspension are then pipetted into the reaction cell's incubation well. An appropriate incubation period follows which allows the formation of microparticle/analyte complexes. The complexes are then pipetted onto the reaction cell's glass fiber capture matrix and a the conjugate comprising an anti-analyte antibody labeled with a signal generating group such as, for example, a fluorophore is also pipetted onto the reaction cell's glass fiber matrix. Microparticle/analyte/conjugate complexes are thusly formed and captured by the glass fiber matrix. Through appropriate means the signal generating group can be excited and the resulting fluorescence, if any, can be measured. The amount of such fluorescence is directly related to the amount of analyte in the test sample.

The following examples are provided to assist in illustrating the invention and not intended to limit the invention. All reagents and equipment necessary for carrying out the examples are commercially available and well known to those skilled in the art.

EXAMPLE 1

Determination of an Optimal Loading Concentration for Fluorescein on Polyacrylamide Hydrazide Polymer Polyacrylamide hydrazide polymer (180,000 MW, 160 hydrazides/polymer) was obtained from the Sigma Chemical Company, St. Louis, Mo. Seven solutions of the polymer were produced all of which contained 10 mg of polymer ($5.55 \times 10^{-5}$ mmoles, $8.89 \times 10^{-3}$ mmoles of hydrazides) dissolved in 2.0 ml of pH 7.0 PBS (0.1N sodium phosphate, 0.1N NaCl). A 6.0 mg/ml stock solution of 5',6'-carboxyfluorescein N-hydroxysuccinimide active ester (signal generating group—available from Molecular Probes, Eugene, Oreg.) in DMF was made and added to the polymer solutions at the following concentrations: 5%, 10%, 15%, 25%, 35%, 75%, and 90% of the total molar quantity of reactive hydrazides present on the polyacrylamide hydrazide polymer. The amounts of fluorescein and DMF used to dissolve the fluorescein are shown below in Table 1.

Each aliquot of signal generating group was then added to a solution of polymer. While the solutions of signal generating group were being added to the polymer, the polymer solutions were stirred and the resulting solutions were stirred at room temperature in the dark for approximately 12 hours.

After the mixing period, each of the seven solutions were purified using Sephadex® 100–300μ mesh gel (available from Sigma Chemical Co., St. Louis, Mo.) in a 1.8 cm×30 cm column. The polyfluorescein polymers were eluted from the column with distilled water and 4.0 ml fractions were collected as the polymers eluted.

The purity of each fraction from each solution was determined by normal phase thin layer chromatography (TLC) using 90/10 $CHCl_3/CH_3OH$ as an eluant. The TLC showed that the first fractions collected contained low molecular weight compounds followed by fractions containing high molecular weight compounds. The fractions containing high molecular weight compounds were combined until (as evidenced by a portable long wavelength ultra-violet lamp) the fractions began showing an $R_f$ value of greater than 0.05–0.1.

The combined fractions were concentrated to 4.87 mg/ml using an Amicon® Centiprep-30 concentrator (Amicon Inc., Danvets, Mass.) equipped with a 30,000 molecular weight cut-off membrane. The concentrator was spun at 3000 RPM for 3 hours.

The concentrated fractions were then repurified using Sephadex® G-25 gel in a 1.8 cm×30 cm column and eluted as above. The resulting fractions were checked for purity, combined and concentrated as above.

The procedure resulted in seven solutions of purified polyfluorescein polymer which had been loaded with different concentrations of signal generating group. These polymeric solutions were then tested for their ability to fluoresce with a fluorescence spectrophotometer. The results of the fluorescence testing are shown below in Table 1 which shows the attempted loading concentration and the fluorescence value associated with the individual loading concentrations. As Table 1 shows, there is an increase in fluorescence until the 90% loading concentration is reached. At a 90% attempted loading quenching begins to occur and the fluorescence value drops. Hence, a 75% attempted loading is optimal and was used to produce a preparative amount of polyacrylamide hydrazide polyfluorescein.

TABLE 1

| Attempted Loading % | Fluorescein (mg) | DMF (μl) | Relative Fluorescence |
| --- | --- | --- | --- |
| 5 | 0.20 | 34 | 40 |
| 10 | 0.41 | 68 | 157 |
| 15 | 0.61 | 102 | 300 |

TABLE 1-continued

| Attempted Loading % | Fluorescein (mg) | DMF (μl) | Relative Fluorescence |
| --- | --- | --- | --- |
| 25 | 1.02 | 169 | 417 |
| 35 | 1.42 | 237 | 529 |
| 75 | 3.05 | 470 | 650 |
| 90 | 3.67 | 610 | 640 |

EXAMPLE 2

Synthesis of Optimal Polyacrylamide Hydrazide Polyfluorescein Polymer

Polyacrylamide hydrazide polymer (180,000 MW, 160 hydrazides/polymer) was obtained from the Sigma Chemical Company. The polymer (50.0 mg, $2.8 \times 10^{-4}$ mmoles polymer, $4.4 \times 10^{-2}$ mmoles hydrazides) was dissolved in 10.0 ml of pH 7.0 PBS via magnetically induced stirring for approximately 7 hours. Then, 15.2 mg ($3.3 \times 10^{-2}$ mmoles) of 5',6'-carboxyfluorescein N-hydroxysuccinimide active ester (available from Molecular Probes), that had been dissolved in 500 μl DMF, was added to the stirring solution of polymer. The resulting reaction solution was stirred at room temperature in the dark for approximately 12 hours.

After mixing, the reaction solution was placed over a Sephadex® 100–300μ mesh size G-25 column (2.5 cm×50 cm) and eluted with distilled/deionized water. As the reaction mixture was running through the column at 2.0 ml/minute, fractions of approximately 400 drops (or approximately 14 ml) were collected. The purity of each fraction was assessed by normal phase TLC using 90/10 $CHCl_3/CH_3OH$ as an eluant. The TLC showed that the first fractions collected contained high molecular weight compounds and that subsequent fractions contained high lower molecular weight compounds. The fractions containing high molecular weight compounds were combined until (as evidenced by a portable long wavelength ultra-violet lamp) the fractions began showing an $R_f$ value of greater than 0.05–0.1. The combined fractions were concentrated to a volume of 10.0 ml using a Cenfiprep-30 concentrator having a molecular weight cutoff of 30,000. The Centiprep-30 concentrator, which contained the combined fractions, was centrifuged at a rate of 3,000 rpm for approximately 3 hours at a temperature of between 15°–30° C.

The concentrated fractions were then repurified using a Sephadex® G-25 column (2.5 cm×50 cm) as above. The resulting fractions were checked for purity and combined based on the results of the TLC and the portable long wavelength ultra-violet lamp testing as specified above. Acceptable fractions were combined and the polymer stock was then reconcentrated using an Amicon® Centiprep-30 concentrator as described above.

An assay to determine the concentration of the polymer stock was done by removing five 2 ml samples and removing the solvent from each in vacuo using a rotary evaporation apparatus. Residual water was removed from each sample using a high vacuum apparatus equipped with a dry ice/isopropanol trap. The resultant samples of red powder were then weighed to determine the concentration of the polymer in mg/ml.

In order to obtain an estimate of how many fluoresceins were actually loaded onto the polymer, standard curves were produced for the carboxyfluorescein polymer and a carboxyfluorescein standard (each of which was in a pH 8.0 PBS).

The curves were produced by determining the absorption (at $\lambda=490$ nm) of the standard and the polymer at several different concentrations. Because the slopes ($\epsilon$) of such curves are representative of the molar absorptivity of a single molecular species (i.e. a free coumarin or a single fluorescent polymer), the ratio of the slopes was used to determine the number of coumarins bound to the polymer. Under identical conditions, an e of 1,459,000 mol$^{-1}$ was determined for the polymer and an e of 36,500 mol$^{-1}$ was determined for the free carboxyfluorescein. Thus, the substitution of carboxyfluorescein onto the polymer was determined to be 40/polymer.

Fluorescence equivalence was also determined for the polymer by comparing the fluorescence emission of the polymer to the fluorescence emission of the free fluorescein. The fluorescence equivalence of the polymer was determined to be 14 carboxyfluoresceins/polymer based on an excitation $\lambda$ of 490 nm and an emission $\lambda$ of 520 nm.

EXAMPLE 3

Synthesis of Polyacrylamide Hydrazide Polycascadeblue Polymer

The optimal loading percentage for loading cascade blue onto polyacrylamide hydrazide was determined as described in Example 1. The optimal attempted loading percentage was found to be 72% of the available hydrazides. In order to produce an optimal fluorescent polymer using cascade blue, cascade blue acyl azide (available from Molecular Probes) was reacted with polyacrylamide hydrazide by the following procedure.

Polyacrylamide hydrazide polymer (180,000 MW, 160 hydrazides/polymer) was obtained from the Sigma Chemical Company. The polymer (20.0 mg, 1.1×10$^{-4}$ mmoles polymer, 1.8×10$^{-2}$ mmoles hydrazides) was dissolved in 4.0 ml of pH 7.0 PBS via magnetically induced stirring for approximately 7 hours. Then, 12.0 mg (1.3×10$^{-2}$ mmoles) of cascade blue acyl azide (available from Molecular Probes, Eugene, Oreg.) was allowed to dissolve in 400 µl DMSO before being added to the stirring solution of polymer. The resulting solution was stirred at room temperature in the dark for 12 hours.

After mixing, the reaction solution was placed over a Sephadex® 100–300µ mesh size G-25 column (2.5 cm×50 cm) and eluted with distilled/deionized water. As the reaction mixture was running through the column at 2.0 ml/minute, fractions of approximately 400 drops (or approximately 14 ml) were collected. The purity of each fraction was assessed by normal phase TLC using 90/10 CHCl$_3$/CH$_3$OH as an eluant. As in Example 2, the fractions containing high molecular weight compounds were combined until (as evidenced by a portable long wavelength ultra-violet lamp) the fractions began showing an R$_f$ value of greater than 0.05–0.1. The combined fractions were concentrated to a volume of 10.0 ml using a Amicon® Centriprep-30 concentrator having a molecular weight cutoff of 30,000. The concentrator, which contained the combined fractions, was centrifuged at a rate of 3,000 rpm for approximately 3 hours at a temperature of between about 15°–30° C.

The concentrated fractions were then repurified using a Sephadex® G-25 column (2.5 cm×50 cm) as above. The resulting fractions were checked for purity and combined based on the results of the TLC and the portable long wavelength ultra-violet lamp testing as specified above. Acceptable fractions were combined and the polymer stock was then reconcentrated using an Amicon® Centriprep-30 concentrator as described above.

An assay for the concentration of the polymer stock was done by removing five 2 ml samples and removing the solvent from each in vacuo using a rotary evaporation apparatus. Residual water was removed from each sample using a high vacuum apparatus equipped with a dry ice/isopropanol trap. The resultant samples of blue powder were then weighed to determine the concentration of the polymer in mg/ml.

In the same manner which was set forth in Example 2, the estimated number of cascade blue molecules loaded onto the polymer was determined. However, because cascade blue absorbs at $\lambda=365$ nm the standard curves were made using a $\lambda=365$ nm. Under identical conditions an e of 460,000 mol$^{-1}$ was determined for the fluorescent polymer and an e of 19,200 mol$^{-1}$ was determined for the cascade blue standard. Thus the number of dyes loaded onto the polymer was determined to be 24/polymer.

EXAMPLE 4

Synthesis of Polyacrylamide Hydrazide Polyaminomethyl Coumarin

The following procedure was used to produce a fluorescent polymer with an equivalent fluorescence of approximately 22 aminomethylcoumarins per polymer.

The polyacrylamide hydrazide polymer (180,000 MW, 160 hydrazides/polymer) used in this Example was obtained from the Sigma Chemical Co., and the 7-amino-4-methylcoumarin-3-acetic acid, succinimidyl ester was obtained from Molecular Probes.

The polymer (100 mg, 5.6×10$^{-4}$ mmols, 8.8×10$^{-2}$ mmols hydrazides) was dissolved in 10.0 ml of pH 7.0 PBS by magnetically induced stirring for approximately 7 hours. The aminomethylcoumarin N-hydroxysuccinimide (14.68 mg or 7.1×10$^{-2}$ mmols dissolved in 600 µl of DMF) was added to the stirring solution of dissolved polymer and the resulting solution was stirred at room temperature in the dark for 12 hours.

An initial purification was performed by loading the above solution on a Sephadex® 100–300µ mesh size G-25 column (2.5 cm×50 cm) and eluting the polymer with distilled/deionized water. Fractions of approximately 14 ml were collected and assessed for purity by normal phase TLC using 90/10 CHCl$_3$/CH$_3$OH as an eluant. As in the earlier Examples, the early chromogenic fractions of high molecular weight were combined until the fractions began showing an R$_f$ value of greater than 0.05–0.1 upon examination with a portable long wave length UV lamp. The combined fractions were concentrated to a volume of 20.0 ml by adding them to a Centiprep-30 concentrator (Amicon®) which had a 30,000 molecular weight cutoff and spinning it at 3,000 rpm for 3 hours.

The concentrated fractions were repurified using a Sephadex® G-25 column (2.5 cm×50 cm) and the resulting fractions were checked for purity using TLC as above. The acceptable fractions were combined and the combined fractions were reconcentrated as above.

The concentration of the concentrated fractions was then determined and an assay was run to determine the number of aminomethylcoumarins bound to the polymer. In order to determine the concentration of the concentrated fractions, samples (4×2 ml) of the concentrated fractions were taken and the solvent was removed from them in vacuo via a rotary evaporatory apparatus. The residual water was removed by a high vacuum apparatus equipped with a dry ice/isopropanol trap. The dried samples were then weighed and the concentration (mg/ml) of the polymer was determined.

Using the method set forth in Example 2, the estimated number of aminomethylcoumarin molecules loaded onto the polymer was determined. However, because aminomethylcoumarin absorbs at λ=325 nm the standard curves were made using a λ=325 nm. Under identical conditions an e of 91,882 mol$^{-1}$ was determined for the fluorescent polymer and an e of 803.5 mol$^{-1}$ was determined for the aminomethylcoumarin standard. Thus the number of dyes loaded onto the polymer was determined to be 114/polymer.

Fluorescence equivalence was also determined for the polymer by comparing the fluorescence emission of the polymer to the fluorescence emission of the free coumarin. The fluorescence equivalence of the polymer was determined to be 22.4 aminomethylcoumarins/polymer based on an excitation λ of 325 and an emission λ of 450.

EXAMPLE 5

Synthesis of Polyacrylamide Hydrazide Polyhydroxymethyl Coumarin

The following procedure was used to produce a fluorescent polymer with an equivalent fluorescence of approximately 40 hydroxycoumarins per polymer.

The polyacrylamide hydrazide polymer (180,000 MW, 160 hydrazides/polymer) used in this Example was obtained from the Sigma Chemical Co., and the 7-hydroxy-4-methylcoumarin-3-acetic acid, succinimidyl ester was obtained from Molecular Probes.

The polymer (50 mg, 2.8×10$^{-4}$ mmols, 4.4×10$^{-2}$ mmols hydrazides) was dissolved in 10.0 ml of pH 7.0 PBS by magnetically induced stirring for approximately 7 hours. The hydroxycoumarin N-hydroxysuccinimide (6.9 mg or 2.1×10$^{-2}$ mmoles dissolved in 500 μl of DMF) was added to the stirring solution of dissolved polymer and the resulting solution was stirred at room temperature in the dark for 12 hours.

An initial purification was performed by loading the above solution on a Sephadex® 100–300μ mesh size G-25 column (2.5 cm×50 cm) and eluting the polymer with distilled/deionized water. Fractions of approximately 14 ml were collected and assessed for purity by normal phase TLC using 90/10 CHCl$_3$/CH$_3$OH as an eluant. As in the earlier Examples, the early chromogenic fractions of high molecular weight were combined until the fractions began showing an R$_f$ value of greater than 0.05–0.1 upon examination with a portable long wave length UV lamp. The combined fractions were concentrated to a volume of 20.0 ml by adding them to a Centiprep-30 concentrator (Amicon®) which had a 30,000 molecular weight cutoff and spinning it at 3,000 rpm for 3 hours.

The concentrated fractions were repurified using a Sephadex® G-25 column (2.5 cm×50 cm) and the resulting fractions were checked for purity using TLC as above. The acceptable fractions were combined and the combined fractions were reconcentrated as above.

The concentration of the concentrated fractions was then determined and an assay was run to determine the number of aminomethylcoumarins bound to the polymer. In order to determine the concentration of the concentrated fractions, samples (4×2 ml) of the concentrated fractions were taken and the solvent was removed from them in vacuo via a rotary evaporatory apparatus. The residual water was removed by a high vacuum apparatus equipped with a dry ice/isopropanol trap. The dried samples were then weighed and the concentration (mg/ml) of the polymer was determined.

Using the method set forth in Example 4, the estimated number of aminomethylcoumarin molecules loaded onto the polymer was determined. Under identical conditions an ε of 209,820 mol$^{-1}$ was determined for the fluorescent polymer and an ε of 2158 mol$^{-1}$ was determined for the hydroxymethylcoumarin standard. Thus the number of dyes loaded onto the polymer was determined to be 100/polymer.

Fluorescence equivalence was also determined for the polymer by comparing the fluorescence emission of the polymer to the fluorescence emission of the free coumarin. The fluorescence equivalence of the polymer was determined to be 40 hydroxymethylcoumarins/polymer based on an excitation λ of 325 and an emission λ of 450.

EXAMPLE 6

Attachment of Polyacrylamide Hydrazide Polyfluorescein to IgG

Initially the carbohydrate region of a mouse monoclonal antibody was oxidized with sodium periodate using the following procedure.

Anti-dansyl antibody (2.05 mg in 1.0 ml TEA buffer, 50 mM triethanolamine, 160 mM NaCl, pH8.0) was placed in an amber colored vial. Sodium periodate (100 μl of a 200 mM solution in TEA buffer) was then added to the vial and the resulting mixture was statically incubated at 2°–8° C. for 1 hr. The reaction mixture was then passed over a Sephadex® G-25 column (1 cm×45 cm, 100–300μ mesh size) at a flow rate of 1–2 ml per minute and eluted with a pH 5.5 acetate buffer (0.1M sodium acetate, 0.1M NaCl). As the column was eluted the eluant from the column was monitored at A$_{280}$ and 1 ml fractions were collected. The elution profile showed two peaks and the fractions from the first peak having an A$_{280}$ of greater than 0.3 were combined. The combined fractions were then concentrated to 2.35 mg/ml (0.8 ml) using an Amicon® Centricon-30 microconcentrator equipped with a 30,000 molecular weight cutoff membrane to yield 1.88 mg of the purified oxidized antibody. The purified antibody was kept at 2°–8° C. and used immediately after oxidation.

The amount of polymer used for conjugation to the antibody was calculated from the molecular weights of the antibody (180,000) and polymer (estimated at 218,000 based on UV assay for fluorescein substitution on the polymer). In this Example, 4.5 mg of the fluorescent polymer from Example 2 was reconstituted in 1.0 ml of pH 4.5 acetate buffer (0.1M sodium acetate, 0.1M NaCl) to form a 4.5 mg/ml solution of polyacrylamide hydrazide polyfluorescein. This solution was then added to 0.8 ml of the 2.35 mg/ml solution of oxidized anti-dansyl antibody to form a conjugation mixture which was gently shaken overnight at a temperature of between about 2°–8° C.

After the conjugation of the antibody to the fluorescent polymer was complete, the conjugation mixture was run over a 1 cm×45 cm column of Sephacryl® S-300 gel (Pharmacia LKB, Sollentuna, Sweden). The conjugated antibody was eluted from the column with pH 8.0 PBS at a flow rate of 1–2 ml per minute. The eluant from the column was collected in 3 ml fractions. The chant was also monitored at A$_{280}$ and the elution profile showed that two peaks were eluted from the column. Fractions from the first peak that had an A$_{280}$ of greater than 0.3 were collected and pooled.

EXAMPLE 7

Synthesis of 6-β-Cyclodextrin Monoaldehyde From Cyclodextrin

The monotosylate derivative of β-cyclodextrin was prepared according to the method of Petter, R. C., et al., *J. Am.*

*Chem. Soc.*, 112, 3360–3868, 1990. The monotosylate derivative was purified by preparative RP-HPLC using a gradient separation at 40.0 ml/min on a Rainin Dynamax™ radial compression column. The gradient used for this separation was as follows: a linear gradient from 90/10 $H_2O/CH_3OH$ by 30 minutes, followed by ramping to 0/100 $H_2O/CH_3OH$ in 35 minutes total elapsed time. The monotosylate eluted at 20.7 minutes using this gradient with UV detection at a $\lambda$ of 230 nm. The solvent was removed at a reduced pressure and the remaining water was removed from the solid by placing it under high vacuum overnight.

The resultant monotosylate (1.0 g, 0.77 mmoles) was then dissolved in 20.0 ml of DMSO. Hunig's base (diisopropylethyl amine 0.5 equivalents of the monotosylate, 0.060 g, 0.38 mmoles) was then added to the monotosylate/DMSO solution and the resultant reaction mixture was heated for approximately 72 hours at a temperature of between 70°–80° C. During the heating period, the reaction mixture was placed under nitrogen. After the heating period the reaction mixture was cooled to room temperature, and a crude product was precipitated with 200 ml of acetone. The reaction mixture was then cooled to 0° C. and the resulting solid was isolated by vacuum filtration.

The isolated solid was resuspended in an amount of room temperature acetone adequate for recrystalization upon cooling to 0° C. The resulting precipitate was recovered again using vacuum filtration. The resuspension and recovery procedure was repeated twice.

The final 6-β-cyclodextrin monoaldehyde product had the following characteristics: PDMS Obs. 1155.5 Calc. 1155.9 $(M+Na^+)$; ESIMS Obs. 1133.9 Calc. 1134.0 $(M+H^+)$; $^1H$ NMR (300 MHz) $d_6$-DMSO $\delta$ 9.7 (s,1H), 5.75 (broad m, 14H), 4.85 (m, 7H), 4.48 (m, 6H), 3.6 (m, 14H), 3.4 (broad m, 7H); 13C NMR (125.6 MHz) crude reaction mixture in $d_6$-DMSO, excluding tosylate peaks. $d_6$-DMSO $\delta$ 198.2, 1201.9, 87.5, 82.5, 81.7, 81.5, 73.072.7, 72.4, 72.0, 68.9, 59.9, 59.6; TLC (1/1 mixture of 10:8:3 n-butanol/ethanol/water and 12:3:4 butanone/methanol/acetic acid): $R_f$ 0.5; IR ($cm^{-1}$).

EXAMPLE 8

Synthesis of Polyacrylamide Hydrazide Polycyclodextrin Polymer

6-β-cyclodextrin monoaldehyde was synthesized as described above in Example 5. Polyacrylamide hydrazide polymer (MW 180,000, 160 hydrazides/polymer) was obtained from the Sigma Chemical Company. The polymer (5.0 mg, $2.28 \times 10^{-5}$ mmoles polymer, $3.65 \times 10^{-3}$ mmoles hydrazides) was dissolved in 1.0 ml pH 7.0 PBS. Another solution, comprising 5.0 mg of 6-β-cyclodextrin monoaldehyde ($4.44 \times 10^{-3}$ mmoles) dissolved in 150 ml of DMSO, was then added to the stirring polymer solution. The resultant solution was then heated to 70° C. for 2 hours. After heating, the solution was allowed to cool to room temperature before it was passed over a Sephadex® G-25 gel filtration column. PBS (pH 7.0) was used to elute the polycyclodextrin polyacrylamide hydrazide polymer from the column. As the polymer was eluting from the column 1.0 ml fractions were collected and analyzed for carbohydrate content using the phenol/sulfuric acid method disclosed in *Analytical Chemistry*, Vol 28, 350–386 (March 1956). The data obtained was used to construct a gel filtration profile for the resultant fractions of polymeric β-cyclodextrin. This gel filtration profile was then compared to a gel filtration profile for monomeric β-cyclodextrin. The comparison revealed most of the polymeric β-cyclodextrin had eluted in fractions 7–11, while most of the monomeric β-cyclodextrin eluted in fractions 9–16. Fractions 7–10 were combined and concentrated using an Amicon® microconcentrator equipped with a 30,000 MW cutoff membrane. The concentrate was diluted with pH 7.0 PBS and reconcentrated 3 times to remove monomeric β-cyclodextrin monoaldehyde. Lack of monomeric β-cyclodextrin monoaldehyde in the filtrate was determined by the phenol/sulfuric acid method of carbohydrate analysis.

EXAMPLE 9

Synthesis of Polylysine Polycyclodextrin Polymer

6-β-cyclodextrin monoaldehyde was synthesized as described above in Example 5. The polylysine polymer (138,000 MW, 1000 lysines/polymer, 5.0 mg, $3.6 \times 10^{-5}$ mmoles polymer, $3.6 \times 10^{-2}$ mmoles amine) is dissolved in 2.0 ml of pH 7.0 PBS. Another solution comprising, 40.8 mg ($3.6 \times 10^{-2}$ mmoles) of 6-β-cyclodextrin monoaldehyde dissolved in 500 ml of DMSO, is then added to the stirring polymer solution. The resultant solution is then stirred for 3 hours at room temperature. After the 3 hour mixing period, a solution of $NaCNBH_3$ (3.6 mmoles) dissolved in 1.0 ml of pH 7.0 PBS is added to the reaction mixture. After 2 hours of mixing at room temperature, the mixture is passed over a Sephadex® G-25 gel filtration column. PBS (pH 7.0) is used to elute the column and 1.0 ml fractions are collected. The fractions are analyzed for carbohydrate content using the phenol/sulfuric acid method. The data obtained is used to construct a gel filtration profile for the resultant polymeric β-cyclodextrin. This gel filtration profile is then compared to a gel filtration profile for monomeric β-cyclodextrin. Those fractions containing polymeric β-cyclodextrin are combined and concentrated using an Amicon® microconcentrator equipped with a 30,000 MW cutoff membrane. The concentrate is diluted (with pH 7.0, 0.1N sodium phosphate, 0.1N NaCl) and reconcentrated 3 times or until no monomeric β-cyclodextrin is observed in the filtrate as indicated by the phenol/sulfuric acid method of carbohydrate analysis.

EXAMPLE 10

Attaching Cyclodextrin Monoaldehydes to Aminated Solid Phases

Using stoichiometric modifications to Example 7, cyclodextrin monoaldehydes can be attached to aminated solid phases. In addition, when derivitizing solid phases, Example 7 is further modified by separating the monomeric cyclodextrin monoaldehyde from the derivatized solid phase by decanting, washing or centrifugation, as opposed to using the size exclusion separation used in Example 7.

EXAMPLE 11

Attachment of Polyacrylamide Hydrazide Polycyclodextrin to Antibody

The polyacrylamide hydrazide polycyclodextrin polymer is attached to an antibody using the same protocol established in Example 4.

EXAMPLE 12

Introduction of Signal Generating Groups Into the Hydrophobic Cavities of Polycyclodextrin Polymers Which are Bound to a Specific Binding member Polyacrylamide hydrazide polycyclodextrin is produced as shown in Example 6. A $10^{-10}M$ to $10^{-6}M$ solution of fluorescein in pH 7.0 PBS is added to a $10^{-10}$M to $10^{-6}$M solution of the polymer obtained from example 6. This solution is then mixed for approximately 2 hours at an ambient temperature. After the mixing period, the solution is passed over a Sephadex® G-25 gel filtration column using pH 7.0 PBS to elute the fluorescent conjugate from the column at a flow rate of between 1–2 ml/min. As the conjugate is eluting from the column fractions of between 1–4 ml are collected. In addition, the $A_{280}$ of the eluant is taken as the conjugate is eluted from the column and fractions from the first peak eluted from the column which have an $A_{280}$ value of greater than 0.3 are combined.

EXAMPLE 13

Comparison Between Commercial Fluorescent Conjugate and Polyacrylamide Hydrazide Polyfluorescein Conjugate In this example, a flow cytometry format was used to make a comparison between the signals generated from currently available commercial conjugates and the conjugate herein provided. The comparison was made between conjugates that are specific for the lymphocyte surface markers CD2, CD3, and LEU4. The commercially available conjugates were FITC conjugates which were either directly specific for the cell surface markers, or AVIDIN FITC conjugates that were specific for BIOTIN primary reagents that were specific for one of the cell surface markers. All of the BIOTIN primary reagents and the CD2-FITC are commercially available from Coulter Inc. (Hialeah, Fla.), while the AVIDIN FITC conjugates are available from Becton-Dickinson Inc. The polyacrylamide hydrazide polyfluorescein conjugates (PAH-F) were prepared according to the methodologies set forth in Example 2 and Example 6. Other reagents used in this Example included pH 7.0 PBS having 0.1% sodium azide and 1.0% bovine serum albumin (BSA) added to the above formulation, and ammonium chloride lysing solution. The lysing solution was prepared as follows:

| Ingredient | Amount (g) |
|---|---|
| NH$_4$Cl | 8.26 |
| KHCO$_3$ | 1.0 |
| NaEDTA | 0.037 |

The ingredients listed above were dissolved in 1.0 liter of distilled water and the resulting solution was adjusted to a pH of 7.3 with Hepes buffer which is available commercially from Sigma Chemical Co., St. Louis, Mo. Before use, the lysing solution was warmed to 41° C.

Protocol

Tubes 1–5, shown below in Table 2, served as control tubes for this example and, except for tube 1 which contained modified PBS exclusively, contained the listed primary or secondary reagent in modified PBS buffer. The primary reagents, or in the case where a conjugate was directly specific for a cell surface marker (tube 6), the secondary reagents, were added to tubes 6–15 in the amounts shown below in Table 2. 200 μl of fresh whole blood was then placed in each of the tubes labeled 6–15 before the contents of each tube were gently vortexed and incubated at room temperature in the dark for 15 minutes. After the incubation, all of the tubes, except tube 6, were washed once in 3 ml of the modified PBS. The washed tubes were then centrifuged for 3 minutes at 500×gravity, the supernatant from these tubes was then aspirated, and the cell pellet was resuspended in the modified PBS.

The secondary reagents (shown in Table 2) were added to their respective tubes, which contained the resuspended pellets, before being vortexed and incubated as above. After the incubation the tubes were treated with the ammonium chloride lysing solution according to the following protocol.

1. 3.0 ml of the lysing solution was added to each tube
2. each tube was thoroughly mixed with a disposable pipette
3. each tube was incubated at room temperature for 7 minutes
4. the tubes were centrifuged for 3 minutes at 2000 rpm
5. all but 100 μl of the supernatants from each tube were aspirated
6. the tubes were vortexed to resuspend the pellets
7. 3.0 ml of PBS having 0.1% sodium azide and 1.0% BSA was then added to the resuspended pellets
8. steps 4–7 were repeated
9. 0.5 ml of PBS having 0.1% sodium azide and 1.0% BSA was then added to the resuspended pellets Tube number 6 was also treated with the ammonium chloride lysing solution according to the protocol set forth above.

The contents of each tube was analyzed using a Facscan II fluorescence activated cell sorter available from Becton-Dickinson Inc. The instrument settings were optimized for visualization on lymphocytes, monocytes and granulocytes on forward verse side scatter parameters. "Quick Cal" beads (available from Flow Cytometry Standards Corporation, Durham, N.C.) were run, as instructed by the accompanying software program, in order to generate a calibration curve. The percent fluorescent events on the histogram was determined for each tube using the three light scatter gates. The MESF values were calculated using the equation generated by the "Quick Cal" software.

Results

The results obtained from tubes 6–15 are shown in Table 3. As an initial matter, since the molecular weight of a PAH-F IgG conjugate is approximately 300,000 and the molecular weight of a FITC IgG conjugate is approximately 150,000, on a molecular weight basis, 1 ug of the PAH-F conjugate is equal to about 2 ug of the FITC conjugate. As evidenced by the data in Table 3, the highly fluorescent conjugate of the instant invention is capable of emitting a signal approximately thirty-five fold stronger than conjugates commercially available. In addition, the binding specificity of the PAH-F conjugate is comparable to that of the FITC conjugate. The signals associated with the granulocytes and monocytes for the FITC conjugates and the PAH-F conjugates are relatively equivalent and thus, serve as evidence that the PAH-F conjugate is at least as specific as the FITC conjugate.

TABLE 2

| Tube # | Primary Reagent | Secondary Reagent |
|---|---|---|
| 1 | modified PBS | — |
| 2 | 5 ug polybiotin | — |
| 3 | — | 2 μg Avidin-FITC |
| 4 | — | 4 μg Avidin-FITC |
| 5 | — | 4 μg antibiotin-PAH-F |
| 6 | — | 2.5 μg CD2-FITC |
| 7 | 5 ug CD2-BIOTIN | 2 μg AVIDIN-FITC |
| 8 | 5 ug CD2-BIOTIN | 4 μg AVIDIN-FITC |
| 9 | 5 ug CD2-BIOTIN | 4 μg ANTIBIO-PAH-F |
| 10 | 5 ug CD2-BIOTIN(T11) | 6 μg mono anti-BIO-PAH-F |
| 11 | 5 ug CD2-BIOTIN(T11) | 4 μg mono anti-BIO-PAH-F |

TABLE 2-continued

| Tube # | Primary Reagent | Secondary Reagent |
|---|---|---|
| 12 | 5 ug CD2-BIOTIN(T11) | 2 μg mono anti-BIO-PAH-F |
| 13 | 5 ug LEU4-BIOTIN | 4 μg Avidin-FITC |
| 14 | 5 ug LEU4-BIOTIN | 6 μg mono-anti-BIO-PAH-F |

EXAMPLE 14

Fluorescence Enhancement of Polymeric Fluorescein by β-Cyclodextrin

Two lots of polyacrylamide hydrazide polyfluorescein were prepared by the method set forth in Example 2. The first lot loaded polyacrylamide hydrazide polymer (180,000 MW, 160 hydrazides/polymer) with 5',6'-carboxyfluorescein N-hydroxysuccinimide active ester at an attempted loading percentage of 10%. The second lot loaded polyacrylamide hydrazide polymer (180,000 MW, 160 hydrazides/polymer) with 5',6'-carboxyfluorescein N-hydroxysuccinimide active ester at an attempted loading percentage of 75%.

The actual number of fluoresceins loaded on the two lots of polymer then was determined by comparing the fluorescence of the polymers to the fluorescence of carboxy fluorescein as above. The number of fluoresceins observed was then determined by UV spectroscopy as per Example 2. From this data, the amount of quenching for each polymer was determined. For example, for lot 1 the number of fluoresceins per polymer was determined to be 11 and the number of fluoresceins observed was 5.5. Thus the fluoresceins on the polymer lot 1 were quenched by approximately 50%.

β-Cyclodextrin was then added to the solutions of polymer so that the β-cyclodextrin was present at a concentration of 0.01M. Following the addition of the cyclodextrin, the number of fluoresceins observed on the polymers was re-determined. Through the addition of β-cyclodextrin to the two lots of fluorescent polymer, the number of fluoresceins observed was increased. The results of this Example are shown in Table 4 wherein $\underline{A}$ is the molar absorptivity, $\underline{B}$ is the number of fluoresceins/polymer, $\underline{C}$ is the number of fluoresceins observed, $\underline{D}$ is the number of fluoresceins observed after the addition of β-cyclodextrin and $\underline{E}$ is the amount of enhancement provided by the 0.01M β-cyclodextrin.

TABLE 3

| Sample | A | B | C | D | E |
|---|---|---|---|---|---|
| carboxy-fluorescein hydrazide | 36,000 | — | — | — | — |
| Lot 1 | 400,000 | 11 | 5.5 | 8.8 | 1.5 |
| Lot 2 | 1,490,000 | 40 | 14 | 28.8 | 1.95 |

EXAMPLE 15

Comparison of Polyfluorescein and Polyfluorescein β-Cyclodextrin Aldehyde Copolymer Polyacrylamide hydrazide polyfluorescein was synthesized as in Example 2. A 3.0 ml portion of the optimized polyacrylamide hydrazide polyfluorescein polymer stock was diluted to 0.7 mg/ml with 0.1N phosphate buffer at pH 5.5 with 0.1N NaCl. 3.0 ml of the diluted polymer was removed to later serve as a control, and 3.0 mg of β-cyclodextrin aldehyde, prepared as in Example 7, was added to the remaining diluted polymer solution. The solid β-cyclodextrin aldehyde was allowed to dissolve in the polymer solution before incubating the newly formed solution overnight at an ambient temperature. After the incubation, the control and polymer/β-cyclodextrin solutions were purified on separate 1×45 cm Sephadex® G-25 size exclusion columns. The elution rate was 45 drops per tube using pH 7.0, 0.1N phosphate, 0.1N NaCl buffer as an elution buffer. The initial polymer concentrations were estimated at 0.26 mg/ml. Based on accurate volume readings and 1 to 10 dilutions of the control and polymer/β-cyclodextrin tubes, polymer concentrations of 0.026 mg/ml, or $1.44 \times 10^{-7}$M were obtained.

A comparison between the fluorescence intensities of the control (non-cyclodextrin derivatized polyacrylamide hydrazide polyfluorescein) and the experiment (cyclodextrin aldehyde derivatized polyacrylamide hydrazide polyfluorescein) was then performed. Specifically, the two solutions were excited at 488 nm and the fluorescence was read at 525 nm. The fluorescence results for the two solutions are shown below in Table 4.

TABLE 4

| Polymer | Fluorescence |
|---|---|
| Polyacrylamide hydrazide polyfluorescein | 108 |
| Polyacrylamide hydrazide polyfluorescein polyβ-cyclodextrin | 138 |

A fluorescence ratio of 138:108 in relative fluorescence intensity was observed for the experiment over the control. Hence, the fluorescence of the experimental polymer was 1.3 times that of the control polymer. This corresponds to a 30% increase in signal for the experimental polymer which translates to a 20 fluoresceins per polymer equivalent as opposed to a 15 fluoresceins per polymer equivalent (as previously shown in TABLE 4, LOT 2, column C). The enhancement in this case being due to the covalently attached β-cyclodextrin rather than non-covalently attached β-cyclodextrin.

EXAMPLE 16

Use of Polyacrylamide Hydrazide Polycoumarin Conjugate to Label and Detect DNA Sequences Polyacrylamide Polycoumarin Synthesis:

According to the synthesis employed in this example, a 45% attempted loading (i.e. an attempt to load 45% of the 160 active sites) of the polyacrylamide hydrazide polymer was performed.

A 20.0 mg/ml solution of polyacrylamide hydrazide polymer (Sigma Chemical Co.) in pH 7.0, 0.01M phosphate, 0.5N NaCl was prepared. 530 ul of a 5.0 mg/ml solution of 7-Amino-4-Methyl-Coumarin-3-Acetic Acid, Succinimidyl ester (Molecular Probes, Inc.) in DMF was then added dropwise to 1.0 ml of the polymer solution which was vigorously stirring. In order to avoid precipitation loss, immediately after the addition of coumarin, the solution was diluted with 2.47 ml of pH 7.0, 0.01M phosphate, 0.5N NaCl buffer and the reaction continued for one hour.

To separate the free coumarin from the polycoumarin polymer, the polymer solution was purified with a 2.5 cm×100 cm Sephadex® G-25 (100–300 um) column, using pH 7.0, 0.01M phosphate, 0.5N NaCl and 5% DMF buffer. The effluents collected from the void volume were characterized and saved for coupling to antibody.

Polyacrylamide Polycoumarin Conjugate Synthesis:

Goat anti-biotin antibody (Pierce Chemical Co., Rockford, Ill.) was diluted to 4.0 mg/ml in TEA buffer (50 mM triethanolamine, 160 mM NaCl, pH 8.0). 110 ul of 200 mM sodium periodate (in TEA buffer) was added to 1.0 ml of the anti-biotin antibody solution, and the resulting solution was incubated for one hour. After the incubation, the solution was passed over a 1.0 cm×45 cm Sephadex® G-25 column using pH 5.5, 0.1M acetate, 0.1M NaCl buffer to remove the excess sodium periodate.

5.0 mg of the polycoumarin solution (prepared above) was then added to 1.0 mg of the oxidized antibody. The antibody/polycoumarin solution was then protected from light and incubated overnight with gentle shaking at 2°–8° C.

After the incubation the antibody-polycoumarin conjugate was passed through a 2.5 cm×100 cm Sephacryl® S300 column to remove free antibody and/or free polycoumarin from the conjugate. The column was eluted with pH 7.0, 0.1M phosphate, 0.5N NaCl buffer. The purified conjugate was then concentrated to approximately 1.0 mg/ml.

The above conjugation procedure was repeated to produce an anti-dansyl conjugate. However, mouse monoclonal anti-dansyl antibody obtained from the University of Pennsylvania(Fan, S. T. and Karush, F. *Molecular Immunology* 21:1023–1029 (1984)) was substituted for the anti-biotin antibody.

Assay Reagents:
1. Test Samples—Two test samples were assayed in this example. Each test sample contained a DNA sequence analyte which was produced by the ligase chain reaction. The sequences were at an initial concentration of $3\times10^{12}$ molecules/reaction in 20 mM N(2-hydroxyethyl)-piperazine-N'-(3-propanesulfonic acid) (HEPPS) buffer pH 7.8. One analyte was SEQ. ID. NO. 1 which was labeled with a carbazole hapten at base position number 1, and biotin haptens at base positions 43 and 52. The other analyte was SEQ. ID. NO. 2 labeled with a carbazole hapten at base position number 1, and two dansyl haptens at base position 51. The sequences were so-labeled by incorporating biotin labeled thymine (Glen Research Corp., Sterling, Va.) into the sequences or labeling the sequences with dansyl phosphoramidite or carbazole phosphoramidite at the specified positions of the sequences.

The conjugation of these haptens to the sequences followed standard b-cyanoethyl-phosphoramidite chemistry which is described in U.S. patent application Ser. No. 625,566 filed Dec. 11 1990, abandoned, Ser. No. 630,908 filed Dec. 20, 1990; Ser. No. 07/808,508, abandoned, and Ser. No. 07/808,839, abandoned, both filed Dec. 17, 1991; as well as Ser. No. 07/858,929 and Ser. No. 07/858,820, both abandoned, both filed Mar. 27, 1992.

2. Capture Reagent—The capture reagent employed in this example was a suspension of anti-carbazole antibody coated microparticles. The particles were synthesized according to the following procedure.

3.3 ml of 30% solid carboxylated microparticles (Seradyn, Inc., Indianapolis, Ind.) was diluted to 10% solids with 6.7 ml of distilled water. The diluted microparticles were mixed with 10.0 gm of Mixed Bed Ion Exchange Resin, Bio-Rex MSZ 501 (D) (from BioRad, Inc., Richmond, Calif.) for 1.5 hours at room temperature. After the incubation, 25.0 ml of 50 mM MES Buffer (2-morpholinoethanesulfonic acid from Sigma, St. Louis, Mo.) pH 4.0 was added to the mixed bed resin/microparticle suspension. The activated microparticles were then separated from the bed resin by vacuum filtration through a coarse frit scintered glass Buchner Funnel. 10.0 ml of 2 mg/ml rabbit anti-carbazole antibody was diluted with 140 ml of 50 mM MES Buffer (pH 4.0) and the diluted antibody was then added to the activated microparticles. The microparticle/antibody suspension was then stirred for 10 minutes at room temperature. Within the 10 minute stirring period, 14.0 ml of 2 mg/ml EDAC [1-ethyl-3-(3-dimethyl aminopropyl)carbodiimide hydrochloride] in distilled water was added to the anti-carbazole antibody/microparticle suspension. This suspension was then stirred overnight at room temperature. The coated Microparticles were placed onto the Membrex Concentrator (Membrex Inc., Fairfield, N.J.) and washed with 600 ml of 20 mM phosphate buffer (containing 0.15N NaCl and 0.1% Tween 20), pH 7.2. The particles were further washed with 500 ml of 50 mM Tris Buffer, pH 8.0. The coated microparticles were then diluted to one liter with 50 mM Tris Buffer, pH 8.0.

3. Indicator Reagent—The indicator reagents employed in this example were the anti-biotin antibody/polycoumarin conjugate and anti-dansyl antibody/polycoumarin conjugate synthesized above.

4. Wash Buffer—The wash buffer employed in this example was LCx line buffer available from Abbott Laboratories, Abbott Park, Ill.

Assay Method:

The assays were run on an IMx® system available from Abbott Laboratories, Abbott Park, Ill. The IMx® system's reagent pack was configured such that the capture reagent was placed in the microparticle bottle position and the indicator reagent was placed in the conjugate bottle position. 0.1 ml of each test sample was placed in individual sample wells of an IMx® system's test wedge. The test wedge was assembled in the IMx® system's carousel and the IMx® was programmed such that it executed the following steps:

1. 40 ul of the microparticle mixture from the microparticle bottle, 110 ul of wash buffer and 50 ul of the test sample were dispensed into the incubation well and allowed to incubate for 514 seconds;

2. 150 ul of the sample/microparticle mixture was then transferred to the glass fiber matrix and washed once with 100 ul of wash buffer and washed a second time with 50 ul of wash buffer;

3. 50 ul of the indicator reagent was then dispensed onto the glass fiber matrix and allowed to incubated for 20 minutes;

4. the glass fiber matrix was then washed three times with 50 ul of wash buffer per wash;

5. the indicator reagent was then excited at a wavelength of 365 nm and the emission was read at 448 nm.

Assay Results:

A net emission of 180 was recorded for the biotin labeled sequence and a net emission of 269 was recorded for the dansyl labeled sequence.

While the invention has been described in detail and with reference to specific embodiments thereof, it will be apparent to one skilled in the art that various changes and modifications may be made without departing from the spirit and scope of the invention. All references to patents or publications in this specification are incorporated herein by reference.

We claim:

1. A method of determining the presence and/or amount of an analyte in a test sample, said method comprising the steps of:
   a. forming conjugate/analyte complexes by contacting said test sample with a highly fluorescent conjugate to form a mixture, wherein said conjugate comprises a specific binding member covalently bound to at least one optimized highly-fluorescent-polymer, said highly-fluorescent-polymer comprising a backbone polymer and fluorescent moieties covalently bound to said backbone polymer;
   b. separating said conjugate/analyte complexes from said mixture; and
   c. detecting a measurable fluorescent signal, wherein the presence and/or amount of said fluorescent signal is related to the amount of said analyte in said test sample, wherein compounds selected from the group consisting of α-cyclodextrin, β-cyclodextrin, γ-cyclodextrin and combinations thereof, are complexed with said fluorescent moieties.

2. A method of determining the presence and/or amount of an analyte in a test sample, said method comprising the steps of:
   a. forming conjugate/analyte complexes by contacting said test sample with a highly fluorescent conjugate to form a mixture, wherein said conjugate comprises a specific binding member covalently bound to at least one optimized highly-fluorescent-polymer, said highly-fluorescent-polymer comprising a backbone polymer, cyclodextrin moieties selected from the group consisting of α-cyclodextrin moieties, β-cyclodextrin moieties, γ-cyclodextrin moieties and combinations thereof covalently bound to said backbone polymer, and fluorescent moieties either covalently bound to said backbone polymer or hosted within said cyclodextrin moieties;
   b. separating said conjugate/analyte complexes from said mixture; and
   c. detecting a measurable fluorescent signal, wherein the presence and/or amount of said fluorescent signal is related to the amount of said analyte in said test sample.

3. The method of claim 2 wherein said specific binding member is an antibody.

4. The method of claim 2 wherein said backbone polymer comprises the residue of an amine functional polymer.

5. The method of claim 4 wherein said amine functional polymer comprises amine functionalities selected from the group consisting of:

a) 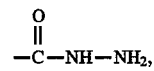

b) —NH$_2$, c) 

wherein R is selected from the group consisting of; C$_1$–C$_3$ alkyl, isopropyl, (CH$_2$)$_2$CO$_2$—, (CH$_2$)$_2$SO$_3^-$, (CH$_2$)$_2$NH$_3^+$, (CH$_2$)$_2$NH$_2^+$(CH$_2$)$_2$SO$_3$ —(CH$_2$)$_2$O(CH$_2$)$_2$O(CH$_2$)$_2$OH, and (CHOH)$_4$CH$_2$OH, and d) combinations thereof.

6. The method of claim 4 wherein said backbone polymer comprises the residue of a polymer selected from the group consisting of: polyacrylamide hydrazide, polyhydrazide, polylysine and combinations thereof.

7. The method of claim 2 wherein said fluorescent moieties are selected from the group consisting of: fluorescein, cascade blue, coumarin, Texas Red™ and phycoerythrin.

8. The method of claim 2 wherein said analyte comprises a nucleic acid sequence.

9. A highly fluorescent conjugate comprising a specific binding member covalently bound to at least one optimized highly-fluorescent-polymer comprising a backbone polymer and fluorescent moieties covalently bound to said backbone polymer, wherein compounds selected from the group consisting of α-cyclodextrin, β-cyclodextrin, γ-cyclodextrin and combinations thereof are complexed with said fluorescent moieties.

10. A highly fluorescent conjugate comprising: a specific binding member covalently bound to at least one optimized highly-fluorescent-polymer, wherein said highly-fluorescent-polymer comprises a backbone polymer, cyclodextrin moieties selected from the group consisting of α-cyclodextrin moieties, β-cyclodextrin moieties, γ-cyclodextrin moieties and combinations thereof covalently bound to said backbone polymer, and fluorescent moieties, said fluorescent moieties either covalently bound to said backbone polymer or hosted within said cyclodextrin moieties.

11. The conjugate of claim 10 wherein the specific binding member is an antibody.

12. The conjugate of claim 10 wherein said backbone polymer comprises the residue of an amine functional polymer.

13. The conjugate of claim 12 wherein said amine functional polymer comprises amine functionalities selected from the group consisting of:

a)

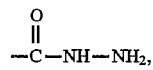

b) $-NH_2$, c)

wherein R is selected from the group consisting of; $C_1$–$C_3$ alkyl, isopropyl, $-(CH_2)_2CO_2^-$, $-(CH_2)_2SO_3^-$, $-(CH_2)_2NH_3^+$, $-(CH_2)_2NH_2^+(CH_2)_2SO_3^-$, $-(CH_2)_2O(CH_2)_2O(CH_2)_2OH$, and $-(CHOH)_4CH_2OH$, and d) combinations thereof.

14. The conjugate of claim 12 wherein said backbone polymer comprises the residue of a polymer selected from the group consisting of: polyacrylamide hydrazide, polyhydrazide, polylysine, and combinations thereof.

15. The conjugate of claim 10 wherein said fluorescent moieties are selected from the group consisting of: fluorescein, cascade blue, coumarin, Texas Red™ and phycoerythrin.

* * * * *